United States Patent
Srinivasan et al.

(10) Patent No.: US 10,703,731 B2
(45) Date of Patent: Jul. 7, 2020

(54) PROCESS FOR THE PREPARATION OF TRISODIUM (4-{[1S,3R)-1-([1,1'-BIPHENYL]-4-YLMETHYL)-4-ETHOXY-3-METHYL-4-OXOBUTYL]AMINO}-4-OXOBUTANOATE)-(N-PETANOYL-N-{[2'-(1H-TETRAZOL-1-1D-5-YL)[1,1'-BIPHENYL]-4-YL]METHYL}-L-VALINATE) AND ITS POLYMORPHS THEREOF

(71) Applicant: MSN LABORATORIES PRIVATE LIMITED, Hyderabad, Telangana (IN)

(72) Inventors: Thirumalai Rajan Srinivasan, Telangana (IN); Eswaraiah Sajja, Telangana (IN); Rajeshwar Reddy Sagyam, Telangana (IN); Rajesham Boge, Telangana (IN); Chkradhar Nandigama, Telangana (IN); Srinivasa Rao Ambati, Telangana (IN)

(73) Assignee: MSN LABORATORIES PRIVATE LIMITED, Hyderabad, Telangana (IN)

( * ) Notice: Subject to any disclaimer, the term of this patent is extended or adjusted under 35 U.S.C. 154(b) by 50 days.

(21) Appl. No.: 16/083,784

(22) PCT Filed: Mar. 6, 2017

(86) PCT No.: PCT/IN2017/000056
§ 371 (c)(1),
(2) Date: Sep. 10, 2018

(87) PCT Pub. No.: WO2017/154017
PCT Pub. Date: Sep. 14, 2017

(65) Prior Publication Data
US 2019/0077775 A1  Mar. 14, 2019

(30) Foreign Application Priority Data

Mar. 7, 2016  (IN) .............................. 201641007802
Sep. 30, 2016  (IN) .............................. 201641033544

(51) Int. Cl.
| | | |
|---|---|---|
| C07D 257/04 | (2006.01) | |
| C07C 233/47 | (2006.01) | |
| C07C 231/12 | (2006.01) | |
| B01D 9/00 | (2006.01) | |
| A61K 47/12 | (2006.01) | |
| A61K 47/38 | (2006.01) | |
| A61K 47/32 | (2006.01) | |
| A61K 47/10 | (2017.01) | |
| A61K 9/10 | (2006.01) | |

(52) U.S. Cl.
CPC .......... *C07D 257/04* (2013.01); *C07C 231/12* (2013.01); *C07C 233/47* (2013.01); *A61K 9/10* (2013.01); *A61K 47/10* (2013.01); *A61K 47/12* (2013.01); *A61K 47/32* (2013.01); *A61K 47/38* (2013.01); *B01D 9/0022* (2013.01); *B01D 9/0027* (2013.01); *C07B 2200/13* (2013.01)

(58) Field of Classification Search
CPC ................................................... C07D 257/04
See application file for complete search history.

(56) References Cited

FOREIGN PATENT DOCUMENTS

WO  WO-2007056546 A1 * 5/2007 ........... C07D 257/04

* cited by examiner

*Primary Examiner* — Joseph R Kosack
(74) *Attorney, Agent, or Firm* — IP Pundit LLC

(57) ABSTRACT

The present invention relates to a process for the preparation of Trisodium (4-{[(1S.3R)-1-([1,1'-biphenyl]-4-yl-methyl)-4-ethoxy-3-methyl-4-oxobutyl]amino}-4-oxo butanoate)-(N-pentanoyl-N-{[2'-(1H-tetrazol-1-id-5-yl)[1,1'-biphenyl]-4-yl]methyl}-L-valinate) represented by the following structural formula-1:

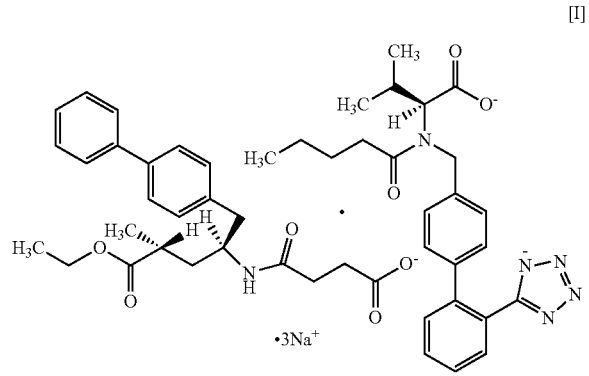

12 Claims, 7 Drawing Sheets

PROCESS FOR THE PREPARATION OF TRISODIUM (4-{[1S,3R)-1-([1,1'-BIPHENYL]-4-YLMETHYL)-4-ETHOXY-3-METHYL-4-OXOBUTYL]AMINO}-4-OXOBUTANOATE)-(N-PETANOYL-N-{[2'-(1H-TETRAZOL-1-1D-5-YL)[1,1'-BIPHENYL]-4-YL]METHYL}- L-VALINATE) AND ITS POLYMORPHS THEREOF

RELATED APPLICATIONS

This application claims the benefit of priority of our Indian patent application numbers IN201641007802 filed on 7 Mar. 2016 and IN201641033544 30 Sep. 2016 which are incorporated herein by reference.

FIELD OF INVENTION

The present invention relates to a process for the preparation of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) represented by the following structural formula-1:

Formula-1

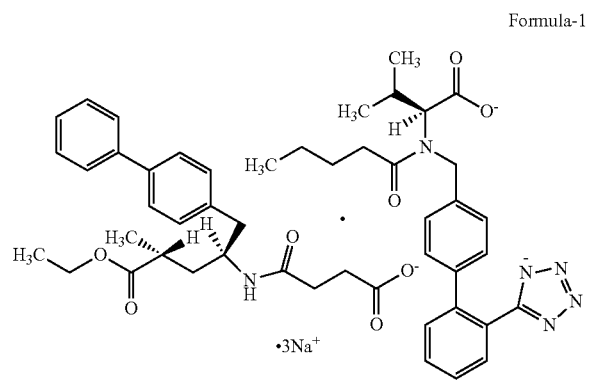 [SMILES: CCOC(=O)[C@H](C)C[C@@H](Cc1ccc(-c2ccccc2)cc1)NC(=O)CCC(=O)[O-] ; CCCCC(=O)N(Cc1ccc(-c2ccccc2-c2nnn[nH]2)cc1)[C@H](C(=O)[O-])C(C)C]

Further, the present invention also relates to solid state forms of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) and process for the preparation thereof.

BACKGROUND OF THE INVENTION

Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) is approved in USA as octadecasodium hexakis-(4-{[(1S,3R)-1-([1,1'-biphenyl]-4-ylmethyl)-4-ethoxy-3-methyl-4-oxobutyl]amino}-4-oxobutanoate)hexakis-(N-pentanoyl-N-{[2'-(1H-tetrazol-1-id-5-yl)[1,1'-biphenyl]-4-yl]methyl}-L-valinate)penta decahydrate under the brand name of "Entresto" which is represented as below:

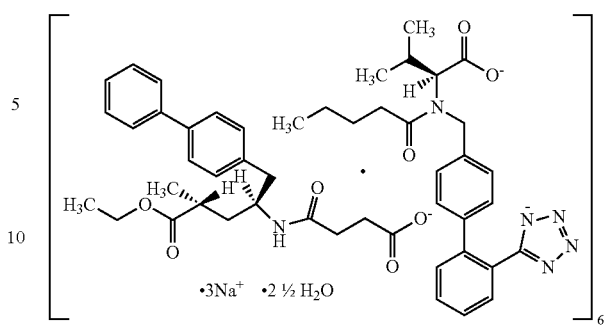

The above said compound can also be represented as "Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) hemipentahydrate", commonly known as "Trisodium Sacubitril Valsartan hemipentahydrate.".

Valsartan/sacubitril (brand name Entresto, previously known as (LCZ696) is a combination drug for use in heart failure developed by Novartis. It consists of the angiotensin receptor blocker valsartan and the neprilysin inhibitor sacubitril, in a 1:1 mixture by molecule count. The combination is sometimes described as an "angiotensin receptor-neprilysin inhibitor" (ARNi). It was approved under the FDA's priority review process on Jul. 7, 2015.

Valsartan/sacubitril is used to treat heart failure in people with reduced left ventricular ejection fraction (LVEF).[3] It is not known whether valsartan/sacubitril is useful for the treatment of heart failure people with normal LVEF.

U.S. Pat. No. 8,877,938B2 disclosed the process for the preparation of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate)hemipentahydrate and its crystalline form.

There is a significant need in the art to develop novel polymorphic forms of the said compound of formula-1 which are stable and having advantageous physical properties such as free flowability, greater stability and greater bioavailability.

BRIEF DESCRIPTION OF THE INVENTION

The first aspect of the present invention is to provide a process for the preparation of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1.

The second aspect of the present invention is to provide a process for the preparation of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1.

The third aspect of the present invention is to provide a process for the preparation of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1.

The fourth aspect of the present invention is to provide a process for the preparation of crystalline form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1.

The fifth aspect of the present invention is to provide novel crystalline form of Trisodium (4-{[(1S,3R)-1-([1,1'-biphenyl]-4-ylmethyl)-4-ethoxy-3-methyl-4-oxobutyl] amino}-4-oxobutanoate)-(N-pentanoyl-N-{[2'-(1H-tetrazol-1-id-5-yl)[1,1'-biphenyl]-4-yl]methyl}-L-valinate) compound of formula-1, herein after designated as crystalline Form-M.

The sixth aspect of the present invention is to provide a process for the preparation of crystalline Form-M of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1.

The seventh aspect of the present invention is to provide novel crystalline form of Trisodium (4-{[(1S,3R)-1-([1,1'-biphenyl]-4-ylmethyl)-4-ethoxy-3-methyl-4-oxobutyl] amino}-4-oxobutanoate)-(N-pentanoyl-N-{[2'-(1H-tetrazol-1-id-5-yl)[1,1'-biphenyl]-4-yl]methyl}-L-valinate) compound of formula-1, herein after designated as crystalline Form-S.

The eighth aspect of the present invention is to provide a process for the preparation of crystalline Form-S of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1.

The ninth aspect of the present invention is to provide a process for the preparation of crystalline Trisodium (4-{[(1S,3R)-1-([1,1'-biphenyl]-4-ylmethyl)-4-ethoxy-3-methyl-4-oxo butyl]amino}-4-oxobutanoate)-(N-pentanoyl-N-{[2'-(1H-tetrazol-1-id-5-yl)[1,1'-biphenyl]-4-yl] methyl}-L-valinate) hemipentahydrate.

The tenth aspect of the present invention is to provide amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1.

The eleventh aspect of the present invention is to provide a process for the preparation of amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1.

The twelfth aspect of the present invention is to provide amorphous solid dispersion comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 and at least one pharmaceutically acceptable excipient.

The thirteenth aspect of the present invention is to provide process for the preparation of amorphous solid dispersion comprising Trisodium (4-{[(1S,3R)-1-([1,1'-biphenyl]-4-ylmethyl)-4-ethoxy-3-methyl-4-oxobutanoate)-(N-pentanoyl-N-{[2'-(1H-tetrazol-1-id-5-yl)[1,1'-biphenyl]-4-yl]methyl}-L-valinate) compound of formula-1 and at least one pharmaceutically acceptable excipient.

DETAILED DESCRIPTION OF THE INVENTION

Figure 1:
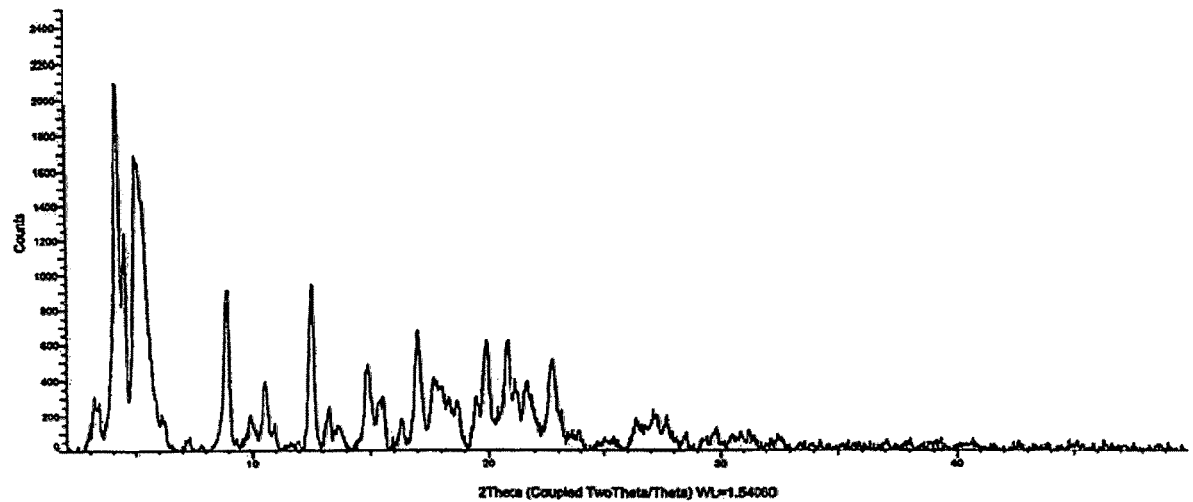
FIG. 1: Illustrates the PXRD pattern of crystalline Form-M of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1.

The "suitable solvent" used in the present invention can be selected from but not limited to "hydrocarbon solvents" such as n-pentane, n-hexane, n-heptane, cyclohexane, pet ether, benzene, toluene, xylene and the like; "ether solvents" such as dimethyl ether, diethyl ether, diisopropyl ether, methyl tert-butyl ether, dimethoxyethane, diethoxyethane, dibutoxyethane, tetrahydrofuran, 1,4-dioxane and the like; "ester solvents" such as methyl acetate, ethyl acetate, n-propyl acetate, isopropyl acetate, n-butyl acetate, isobutyl acetate, tert-butyl acetate and the like; "polar-aprotic solvents" such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcohol solvents" such as methanol, ethanol, n-propanol, iso-propanol, n-butanol, iso-butanol, tert-butanol, n-pentanol, ethane-1,2-diol, propane-1,2-diol, alkyl ethers of ethylene glycol or propylene glycol selected from but not limited to ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, diethylene glycol mono-n-butyl ether and the like; "polar solvents" such as water; formic acid, acetic acid or mixtures thereof.

The term "suitable base" used in the present invention refers to "inorganic bases" selected from "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, lithium methoxide, lithium ethoxide, sodium tert.butoxide, potassium tert.butoxide, lithium tert.butoxide and the like; "alkali metal hydrides" such as sodium hydride, potassium hydride, lithium hydride and the like; "alkali metal amides" such as sodium amide, potassium amide, lithium amide and the like; alkali metal and alkali earth metal salts of acetic acid such as sodium acetate, potassium acetate, magnesium acetate, calcium acetate and the like; ammonia; "organic bases" like dimethylamine, diethylamine, diisopropyl mine, diisopropylethylamine, diisobutylamine, triethylamine, triisopropyl amine, tributylamine, tert.butyl amine, pyridine, 4-dimethylaminopyridine (DMAP), imidazole, N-methylimidazole, 1,8-diazabicyclo[5.4.0] undec-7-ene (DBU), 1,5-diazabicyclo[4.3.0]non-5-ene (DBN), N-methylmorpholine (NMM), 1,4-diazabicyclo[2.2.2]octane (DABCO), 2,6-lutidine and the like; "organolithium bases" such as methyl lithium, n-butyl lithium, lithium diisopropylamide (LDA) and the like; "organosilicon bases" such as lithium hexamethyldisilazide (LiHMDS), sodium hexamethyldisilazide (NaHMDS), potassium hexamethyldisilazide (KHMDS) and the like or their mixtures.

The first aspect of the present invention provides process for the preparation of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, comprising of:
a) Reacting the (2R,4S)-5-([1,1'-biphenyl]-4-yl)-4-((tert-butoxycarbonyl)amino)-2-methylpentanoic acid compound of formula-2 with thionyl chloride in ethanol solvent to provide (2R,4S)-ethyl 5-([1,1'-biphenyl]-4-yl)-4-amino-2-methyl pentanoate hydrochloride compound of formula-3,
b) optionally, purifying the compound of formula-3 from a suitable solvent,
c) reacting the compound of formula-3 with succinic anhydride in presence of a suitable base in a suitable solvent to provide 4-(((2S,4R)-1-([1,1'-biphenyl]-4-yl)-5-ethoxy-4-methyl-5-oxopentan-2-yl)amino)-4-oxobutanoic acid compound of formula-4,
d) treating the compound of formula-4 in-situ with tromethamine in a suitable solvent to provide tromethamine salt of 4-(((2S,4R)-1-([1,1'-biphenyl]-4-yl)-5-ethoxy-4-methyl-5-oxopentan-2-yl)amino)-4-oxobutanoic acid compound of formula-5,
e) treating the compound of formula-5 with a suitable acid in a suitable solvent followed by treating the obtained compound with a suitable sodium source in a suitable solvent to provide mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6,
f) optionally purifying the obtained compound using a suitable solvent or mixture of solvents to provide pure compound of formula-6,
g) treating the (S)-2-(N-((2'-(1H-tetrazol-5-yl)-[1,1'-biphenyl]-4-yl)methyl)pentan amido)-3-methylbutanoic acid compound of formula-8 with a suitable sodium source in a suitable solvent to provide disodium salt of (S)-2-(N-((2'-(1H-tetrazol-5-yl)-[1,1'-biphenyl]-4-yl)methyl)pentanamido)-3-methylbutanoic acid compound of formula-7,
h) reacting the compound of formula-6 obtained in step-(e) or step-(f) with the compound of formula-7 obtained in step-(g) in a suitable solvent to provide trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1.

Wherein, in step-(c) the suitable base is selected from organic base or inorganic base.

In step-(e) & (g) the suitable sodium source is selected from hydrates, hydroxides, carbonates or bicarbonates of sodium.

In step-e) the suitable acid is selected from acetic acid, formic acid, dil. HCl and the like;

In step-(b) to (h) the suitable solvent is selected from alcohol solvents, ketone solvents, ester solvents, hydrocarbon solvents, nitrile solvents, ether solvents, chloro solvents, polar aprotic solvents, polar solvents like water or mixture thereof.

The preferred embodiment of the present invention provides a process for the preparation of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-

(1H-tetrazol-1-id-5-yl)[1,1'-biphenyl]-4-yl]methyl}-L-valinate) compound of formula-1, comprising of:
  a) Reacting the (2R,4S)-5-([1,1'-biphenyl]-4-yl)-4-((tert-butoxycarbonyl)amino)-2-methylpentanoic acid compound of formula-2 with thionyl chloride in ethanol to provide (2R,4S)-ethyl5-([1,1'-biphenyl]-4-yl)-4-amino-2-methylpentanoate hydrochloride compound of formula-3,
  b) purifying the compound of formula-3 from methyl tertiary butyl ether to provide pure compound of formula-3,
  c) reacting the compound of formula-3 with succinic anhydride in presence of triethylamine in dichloromethane to provide 4-(((2S,4R)-1-([1,1'-biphenyl]-4-yl)-5-ethoxy-4-methyl-5-oxopentan-2-yl)amino)-4-oxobutanoic acid compound of formula-4,
  d) treating the compound of formula-4 in-situ with tromethamine in ethylacetate to provide tromethamine salt of 4-(((2S,4R)-1-([1,1'-biphenyl]-4-yl)-5-ethoxy-4-methyl-5-oxopentan-2-yl)amino)-4-oxobutanoic acid compound of formula-5,
  e) treating the compound of formula-5 with dil. HCl in methyl tertiary butyl ether followed by treating the obtained compound with aqueous sodium hydroxide in acetonitrile to provide mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6,
  f) purifying the obtained compound using methyl tertiary butyl ether to provide pure compound of formula-6,
  g) treating the (S)-2-(N-((2'-(1H-tetrazol-5-yl)-[1,1'-biphenyl]-4-yl)methyl)pentan amido)-3-methylbutanoic acid compound of formula-8 with aqueous sodium hydroxide in acetone to provide disodium salt of (S)-2-(N-((2'-(1H-tetrazol-5-yl)-[1,1'-biphenyl]-4-yl)methyl)pentanamido)-3-methyl butanoic acid compound of formula-7,
  h) reacting the compound of formula-6 obtained in step-(e) or step-(f) with the compound of formula-7 obtained in step-(g) in methanol to provide Trisodium (4-{[(1S,3R)-1-(([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1.

The second aspect of the present invention provides a process for the preparation of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, comprising of:
  a) Reacting the tromethamine salt of 4-(((2S,4R)-1-([1,1'-biphenyl]-4-yl)-5-ethoxy-4-methyl-5-oxopentan-2-yl)amino)-4-oxobutanoic acid compound of formula-5 with a suitable acid in a suitable solvent to provide 4-(((2S,4R)-1-([1,1'-biphenyl]-4-yl)-5-ethoxy-4-methyl-5-oxopentan-2-yl)amino)-4-oxobutanoic acid compound of formula-4,
  b) reacting the obtained compound with (S)-2-(N-((2'-(1H-tetrazol-5-yl)-[1,1'-biphenyl]-4-yl)methyl)pentanamido)-3-methylbutanoic acid compound of formula-8 in presence of a suitable sodium source in a suitable solvent to provide Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1,
  c) adding suitable solvent to the obtained compound,
  d) stirring the reaction mixture,
  e) filtering the reaction mixture and distilling off the solvent from the filtrate to get amorphous compound of formula-1.

Wherein, in step-(b) the suitable sodium source is selected from hydrates, hydroxides, carbonates or bicarbonates of sodium.

In step-a) the suitable acid is selected from acetic acid, formic acid, dil. HCl and the like;

In step-(a) to (c) the suitable solvent is same as defined in first aspect of the present invention.

The preferred embodiment of the present invention provides a process for the preparation of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, comprising of:
  a) Reacting the tromethamine salt of 4-(((2S,4R)-1-([1,1'-biphenyl]-4-yl)-5-ethoxy-4-methyl-5-oxopentan-2-yl)amino)-4-oxobutanoic acid compound of formula-5 with dil. HCl in methyl tertiary butyl ether and water to provide 4-(((2S,4R)-1-([1,1'-biphenyl]-4-yl)-5-ethoxy-4-methyl-5-oxopentan-2-yl)amino)-4-oxobutanoic acid compound of formula-4,
  b) reacting the obtained compound with (S)-2-(N-((2'-(1H-tetrazol-5-yl)-[1,1'-biphenyl]-4-yl)methyl)pentanamido)-3-methylbutanoic acid compound of formula-8 in presence of aqueous sodium hydroxide in acetonitrile to provide Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1,
  c) adding aqueous methanol to the obtained compound,
  d) stirring the reaction mixture,
  e) filtering the reaction mixture and distilling off the solvent from the filtrate to get amorphous compound of formula-1.

The third aspect of the present invention provides a process for the preparation of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1, comprising of:
  a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-[1,1'-biphenyl]-4-yl)methyl) pentanamido)-3-methylbutanoic acid compound of formula-7 in a suitable solvent,
  b) stirring the reaction mixture,
  c) filtering the reaction mixture and distilling off the solvent from the filtrate to get amorphous compound of formula-1.

Wherein, the suitable solvent used in step-(a) is same as defined in first aspect of the present invention.

The preferred embodiment of the present invention provides a process for the preparation of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1 comprising of:
  a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-

[1,1'-biphenyl]-4-yl)methyl) pentanamido)-3-methylbutanoic acid compound of formula-7 in aqueous methanol, b) stirring the reaction mixture for 30 minutes, c) filtering the reaction mixture and distilling off the solvent from the filtrate to get amorphous compound of formula-1.

The fourth aspect of the present invention provides a process for the preparation of crystalline form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1, comprising of:

a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-[1,1'-biphenyl]-4-yl)methyl) pentanamido)-3-methylbutanoic acid compound of formula-7 in a suitable solvent, b) stirring the reaction mixture, c) filtering the solid and drying to get crystalline compound of formula-1.

Wherein, the suitable solvent used in step-(a) is same as defined in first aspect of the present invention.

The preferred embodiment of the present invention provides a process for the preparation of crystalline compound of formula-1 comprising of:

a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-[1,1'-biphenyl]-4-yl)methyl) pentanamido)-3-methylbutanoic acid compound of formula-7 in methyl tertiary butyl ether, b) stirring the reaction mixture for 30 minutes, c) filtering the solid and drying to get crystalline compound of formula-1.

The fifth aspect of the present invention provides a novel crystalline form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, herein after designated as crystalline Form-M.

Further, the crystalline Form-M of compound of formula-1 characterized by its PXRD pattern having characteristic peaks at 3.1, 3.3, 4.2, 4.5, 5.0, 6.1, 8.9, 9.9, 10.5, 10.9, 12.5, 13.2, 14.9, 15.5, 16.3, 17.0, 17.7, 18.6, 19.5, 19.9, 20.8, 21.6, 22.7, 26.3 and 27.2±0.2° of 2-theta values. The said crystalline form-M is further characterized by its PXRD pattern as illustrated in FIG. 1.

The sixth aspect of the present invention provides a process for the preparation, of crystalline Form-M of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1, comprising of:

a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-[1,1'-biphenyl]-4-yl)methyl) pentanamido)-3-methylbutanoic acid compound of formula-7 in a suitable solvent, b) stirring the reaction mixture, c) filtering the solid and drying to get crystalline Form-M of compound of formula-1.

Wherein, the suitable solvent used in step-(a) is same as defined in first aspect of the present invention.

The seventh aspect of the present invention provides a novel crystalline form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, herein after designated as crystalline Form-S.

Figure 5:
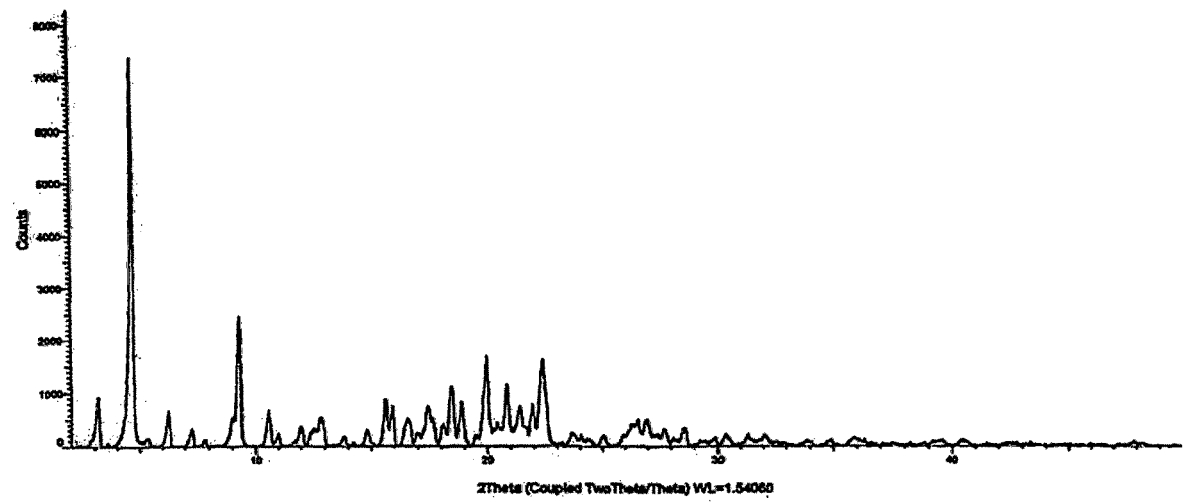
FIG. 5: Illustrates the PXRD pattern of crystalline Form-S of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1.

Further, the crystalline Form-S of compound of formula-1 characterized by its PXRD pattern having characteristic peaks at 3.1, 4.6, 6.2, 7.2, 9.2, 10.5, 11.80, 12.5, 12.8, 15.8, 16.5, 17.5, 18.4, 18.8, 19.9, 20.8, 21.3, 21.9, 22.3 and 25.0±0.20 of 2-theta values. The said crystalline form-S is further characterized by its PXRD pattern as illustrated in FIG. 5.

The eighth aspect of the present invention provides a process for the preparation of crystalline Form-S of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1, comprising of:

a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-[1,1'-biphenyl]-4-yl)methyl) pentanamido)-3-methylbutanoic acid compound of formula-7 in a suitable solvent under nitrogen atmosphere, b) stirring the reaction mixture, c) filtering the solid and drying to get crystalline Form-S of compound of formula-1.

Wherein, the suitable solvent used in step-(a) is same as defined in first aspect of the present invention.

The preferred embodiment of the present invention is to provide a process for the preparation of crystalline Form-S of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1 comprising of:

a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-[1,1'-biphenyl]-4-yl)methyl) pentanamido)-3-methylbutanoic acid compound of formula-7 in n-Heptane at 0 to 5° C. under nitrogen atmosphere, b) stirring the reaction mixture for 2 hours at 0 to 5° C., c) filtering the solid and drying to get crystalline Form-S of compound of formula-1.

The ninth aspect of the present invention provides a process for the preparation of crystalline Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) hemipentahydrate comprising of:

a) Reacting the mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 with disodium salt of (S)-2-(N-((2'-(1H-tetrazol-5-yl)-[1,1'-biphenyl]-4-yl)methyl) pentanamido)-3-methylbutanoic acid compound of formula-7 in aqueous methanol, b) stirring the reaction mixture for 90 minutes,
c) isolating the solid from acetonitrile to get the crystalline Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) hemipentahydrate.

The tenth aspect of the present invention is to provide amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1.

The eleventh aspect of the present invention is to provide a process for the preparation of amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, comprising of:
a) Dissolving the Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in a suitable solvent or mixture of solvents,
b) optionally filtering the reaction mixture,
c) removing the solvent from the reaction mixture to provide amorphous form of compound of formula-1.

Wherein, in step-a) the suitable solvent can be selected from but not limited to chloro solvents, ketone solvents, $C_1$-$C_6$ alcohol solvents, ester solvents, nitrile solvents, ether solvents or their mixtures; and the dissolution of compound of formula-1 in a suitable solvent or mixture of solvents can be carried out at 25-30° C. or by heating the reaction mixture to a temperature ranging from 30° C. to reflux temperature of the solvents employed;

In step-c) suitable techniques which may be used for the removal of solvent from the reaction mixture includes but not limited to evaporation, evaporation under reduced pressure, flash evaporation, vacuum drying, concentrating the reaction mixture, atmospheric distillation, vacuum distillation, distillation by using a rotational distillation device such as a Buchi Rotavapor, agitated thin film drying (ATFD), melt extrusion, spray drying, freeze drying (lyophilization), spray-freeze drying, addition of suitable anti-solvent to the reaction mixture followed by filtration of the precipitated solid, cooling the clear solution to lower temperatures such as below 20° C. to precipitate the solid followed by filtration or by any other suitable techniques.

The solvent may be removed at temperatures ranging from 25° C. to 100° C. optionally under reduced pressures.

The preferred embodiment of the present invention provides a process for the preparation of amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, comprising of:
a) Dissolving the Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in methanol,
b) filtering the reaction mixture,
c) distilling off the solvent from the filtrate to provide amorphous form of compound of formula-1.

The preferred embodiment of the present invention provides a process for the preparation of amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, comprising of:
a) Dissolving the Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in a mixture of dichloromethane and methanol,
b) filtering the reaction mixture,
c) distilling off the solvent from the filtrate to provide amorphous form of compound of formula-1.

The preferred embodiment of the present invention provides a process for the preparation of amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1, comprising of:
a) Dissolving the Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in methanol,
b) filtering the reaction mixture,
c) spray drying the filtrate obtained in step-b) to provide amorphous form of compound of formula-1.

Figure 6:
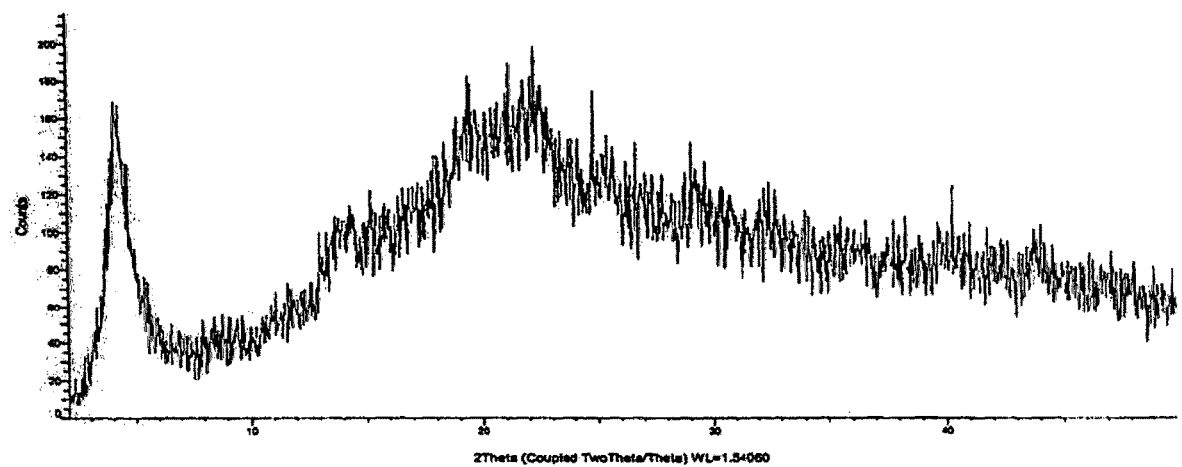
FIG. 6: Illustrates the PXRD pattern of amorphous form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1 obtained according to the process disclosed in Example-1 of U.S. Pat. No. 8,877,938.

The present inventors have repeated the process disclosed in Example-1 of U.S. Pat. No. 8,877,938 and characterized the obtained glossy solid as amorphous form. The PXRD pattern of the obtained compound and the PXRD pattern of amorphous form of compound of formula-1 obtained from the present invention is similar to each other. Further, the PXRD pattern of the compound obtained from Example-1 of U.S. Pat. No. 8,877,938 of illustrated in FIG. 6.

The twelfth aspect of the present invention is to provide amorphous solid dispersion comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 and at least one pharmaceutically acceptable excipient.

Wherein, the excipient is selected from but not limited to polyvinylpyrrolidone (povidone or PVP), polyvinylpolypyrrolidone, polysorbate, cross linked polyvinyl pyrrolidone (crospovidone), polyethylene glycol (macrogol or PEG), polyvinyl alcohol, polyvinyl chloride, polyvinyl acetate, propylene glycol, cellulose, cellulose acetate phthalate (CAP), methyl cellulose, carboxymethyl cellulose (CMC, its sodium and calcium salts), carboxymethylethyl cellulose (CMEC), ethyl cellulose, hydroxymethyl cellulose, ethyl hydroxyethyl cellulose, hydroxyethylcellulose, hydroxypropyl cellulose (HPC), hydroxypropyl cellulose acetate succinate (HPCAS), hydroxypropyl methyl cellulose (hypromellose or HPMC), hydroxypropyl methylcellulose acetate succinate (HPMC-AS), hydroxyethyl methyl cellulose succinate (HEMCS), hydroxypropyl methylcellulose phthalate (HPMC-P), hydroxypropyl methylcellulose acetate phthalate, microcrystalline cellulose (MCC), cross linked sodium carboxymethyl cellulose (croscarmellose sodium), cross linked calcium carboxymethyl cellulose, magnesium stearate, aluminium stearate, calcium stearate, magnesium carbonate, talc, iron oxide (red, yellow, black), stearic acid, dextrates, dextrin, dextrose, sucrose, glucose, xylitol, lactitol, sorbitol, mannitol, maltitol, maltose, raffinose, fructose, maltodextrin, anhydrous lactose, lactose monohydrate, starches such as maize starch or corn starch, sodium starch glycolate, sodium carboxymethyl starch, pregelatinized starch, gelatin, sodium dodecyl sulfate, edetate disodium, sodium phosphate, sodium lauryl sulfate, triacetin, sucralose, calcium phosphate, polydextrose, α-, β-, γ-cyclodextrins, sulfobutylether beta-cyclodextrin, sodium stearyl fumarate, fumaric acid, alginic acid, sodium alginate, propylene glycol alginate, citric acid, succinic acid, carbomer, docusate sodium, glyceryl behenate, glyceryl stearate, meglumine, arginine, polyethylene oxide, polyvinyl acetate phthalates and the like.

The thirteenth aspect of the present invention is to provide process for the preparation of amorphous solid dispersion comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 and at least one pharmaceutically acceptable excipient. The said process comprising of:
a) Dissolving the Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 and at least one excipient in a suitable solvent or mixture of solvents at a suitable temperature,
b) removing the solvent from the reaction mixture to provide amorphous solid dispersion comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 and an excipient.

Wherein, in step-a) the suitable excipient is same as defined in the third aspect of the present invention;

the suitable solvent is same as defined in step-a) of the second aspect of the present invention; the suitable temperature ranges from 0° C. to reflux temperature of the solvent used;

After dissolving the compound of formula-1 and excipient in the solvent system, the solution may optionally be treated with charcoal or any other suitable material to remove color and/or to clarify the solution;

In step-b) the suitable techniques which may be used for the removal of solvent from the reaction mixture are same as defined in step-c) of the second aspect of the present invention;

The solvent may be removed at temperatures ranging from 25° C. to 100° C. optionally under reduced pressures.

In the present invention, the ratio of the amount of weight of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 within the solid dispersion to the amount by weight of the excipient therein ranges from but not limited to about 1:0.05 to about 1:5.

The preferred embodiment of the present invention provides a process for the preparation of amorphous solid dispersion of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in combination with polyvinyl pyrrolidine (PVP K-30), comprising of:
a) Dissolving the compound of formula-1 and PVP K-30 in a mixture of dichloromethane and methanol at 25-30° C.,
b) stirring the reaction mixture,
c) filtering the reaction mixture,
d) distilling off the solvent from the filtrate to provide amorphous solid dispersion of compound of formula-1 in combination with polyvinyl pyrrolidine (PVP K-30).

The another preferred embodiment of the present invention provides a process for the preparation of amorphous solid dispersion of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in combination with HPMC, comprising of:
a) Dissolving the compound of formula-1 and HPMC in a mixture of dichloromethane and methanol at 25-30° C.,
b) stirring the reaction mixture,
c) filtering the reaction mixture,
d) distilling off the solvent from the filtrate to provide amorphous solid dispersion of compound of formula-1 in combination with HPMC.

The another preferred embodiment of the present invention provides a process for the preparation of amorphous solid dispersion of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in combination with HPMC-AS, comprising of:
a) Dissolving the compound of formula-1 and HPMC-AS in a mixture of dichloromethane and methanol at 25-30° C.,
b) stirring the reaction mixture,
c) filtering the reaction mixture,
d) distilling off the solvent from the filtrate to provide amorphous solid dispersion of compound of formula-1 in combination with HPMC-AS.

The another preferred embodiment of the present invention provides a process for the preparation of amorphous solid dispersion of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 in combination with HPC, comprising of:
a) Dissolving the compound of formula-1 and HPC in a mixture of dichloromethane and methanol at 25-30° C.,
b) stirring the reaction mixture,
c) filtering the reaction mixture,
d) distilling off the solvent from the filtrate to provide amorphous solid dispersion of compound of formula-1 in combination with HPC.

The Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 utilized as starting material in the present invention can be prepared by the process disclosed in the present invention (or) any of the processes known in the art.

The solid state forms of compound of formula-1 of the present invention are useful for the preparation of various pharmaceutical compositions formulated in a manner suitable for the route of administration to be used where at least a portion of compound of formula-1 is present in the composition in particular polymorphic form mentioned.

The crystalline Form-M, Form-S and crystalline compound of formula-1 obtained from the present invention can also be used for the preparation of amorphous form of compound of formula-1.

Further, the crystalline Form-M, Form-S & amorphous form of compound of formula-1 obtained from the present invention is useful in the preparation of pharmaceutical composition.

Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) compound of formula-1 produced by the present invention can be further micronized or milled in a conventional techniques to get the desired particle size to achieve desired solubility profile based on different forms of pharmaceutical composition requirements. Techniques that may be used for particle size reduction include, but not limited to ball, roller and hammer mills, and jet mills. Milling or micronization may be performed before drying, or after the completion of drying of the product.

The invention also encompasses pharmaceutical compositions comprising compound of formula-1 or salts thereof of the present invention. As used herein, the term "pharmaceutical compositions" or "pharmaceutical formulations" include tablets, pills, powders, liquids, suspensions, emulsions, granules, capsules, suppositories, or injection preparations.

P-XRD Method of Analysis:

PXRD analysis of compound of formula-1 was carried out by using BRUKER/D8 ADVANCE diffractometer using Cu Kα radiation of wavelength 1.5406 A° and continuous scan speed of 0.03°/min.

The process of the present invention is schematically represented as below:

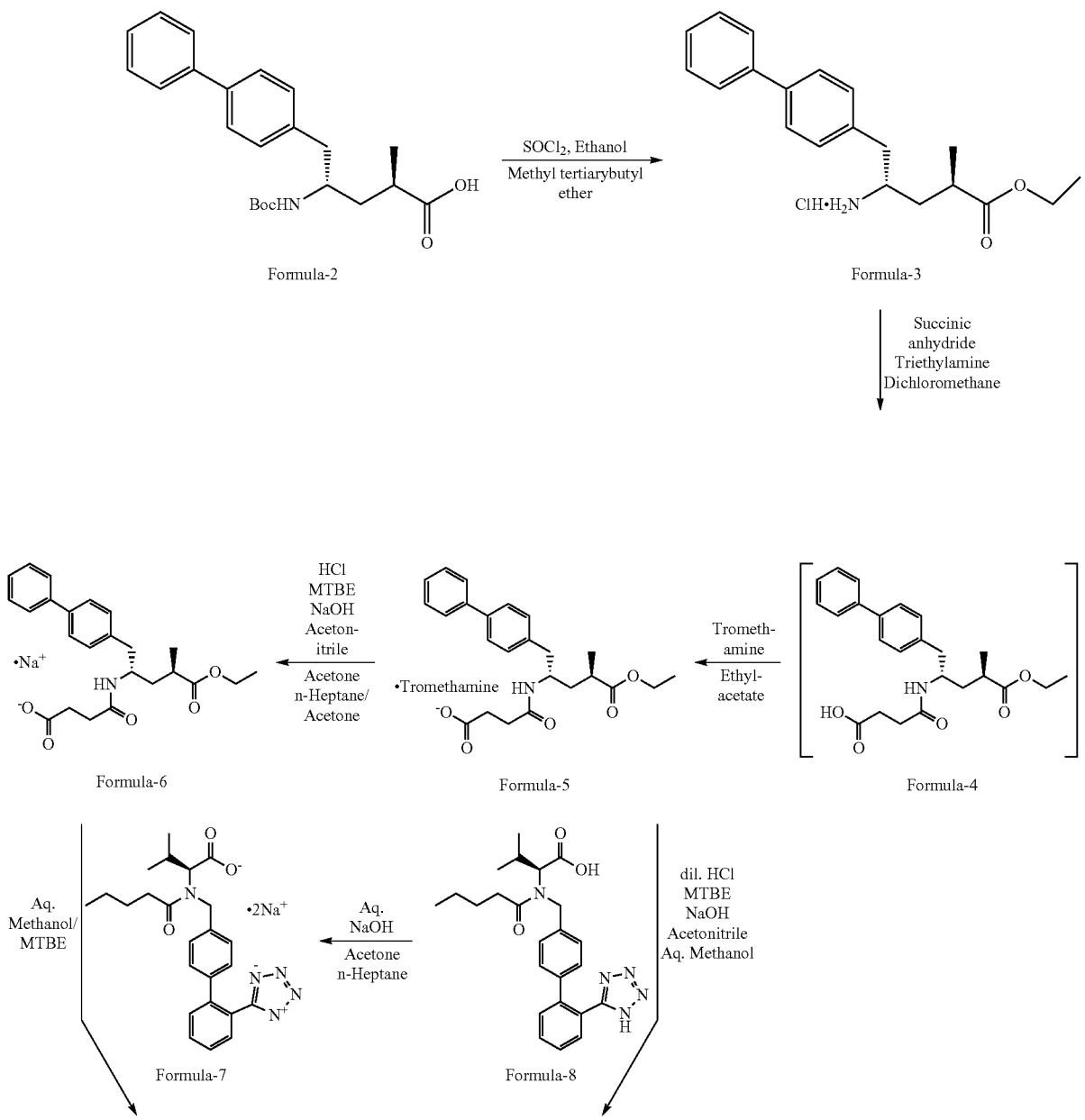

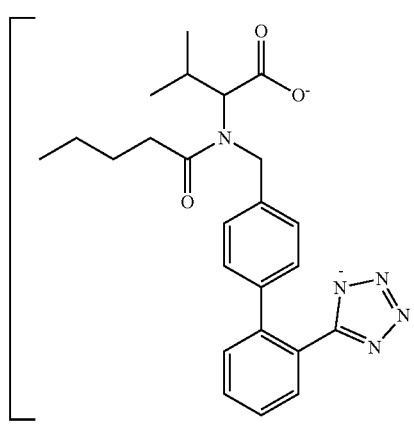 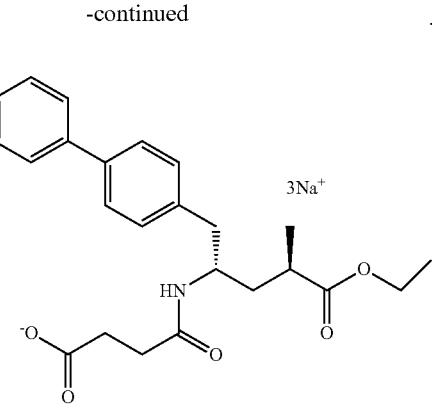

Formula-I

The best mode of carrying out the present invention is illustrated by the below mentioned examples. These examples are provided as illustration only and hence should not be construed as limitation to the scope of the invention.

EXAMPLES

Example-1: Preparation of (2R,4S)-ethyl 5-([1,1'-biphenyl]-4-yl)-4-amino-2-methyl pentanoate hydrochloride (Formula-3)

Thionyl chloride (49.4 ml) was added to a precooled solution containing ethanol (600 ml) and (2R,4S)-5-([1,1'-biphenyl]-4-yl)-4-((tert-butoxycarbonyl)amino)-2-methyl-pentanoic acid compound of formula-2 (200 gms) at 0-5° C. Heated the reaction mixture to 55-60° C. and stirred for 6 hours at the same temperature. Distilled off the solvent completely under reduced pressure and co-distilled with methyl tertiary butyl ether. Cooled the reaction mixture to 25-30° C. Methyl tertiary butyl ether (1400 ml) was added to the obtained compound. Heated the reaction mixture to 50-55° C. and stirred for 30 minutes at the same temperature. Cooled the reaction mixture to 25-30° C. and stirred for 1 hour at the same temperature. Filtered the precipitated solid, washed with methyl tertiary butyl ether and dried to get the title compound.

Yield: 172.3 gms; M.R: 150-158° C.; Purity by HPLC: 99.46%.

Example-2: Preparation of Tromethamine Salt of 4-(((2S,4R)-1-([1,1'-biphenyl]-4-yl)-5-ethoxy-4-methyl-5-oxopentan-2-yl)amino)-4-oxobutanoic acid (Formula-5)

Succinic anhydride (43.14 gms) was added to a mixture of dichloromethane (300 ml) and (2R,4S)-ethyl 5-([1,1'-biphenyl]-4-yl)-4-amino-2-methylpentanoate hydrochloride compound of formula-3 (100 gms) at 25-30° C. Triethyl amine (60.5 ml) was slowly added to the reaction mixture at 25-30° C. and stirred for 3 hours at the same temperature. Water was added to the reaction mixture at 25-30° C. and stirred for 15 minutes at the same temperature. Separated the organic and aqueous layers and extracted the aqueous layer with dichloromethane. Combined both the organic layers and washed with water. Distilled off the solvent completely from the organic layer and co-distilled with ethyl acetate under reduced pressure. Ethyl acetate (600 ml) was added to the obtained compound at 25-30° C. Tromethamine (38.2 gms) was added to the reaction mixture at 25-30° C. Heated the reaction mixture to 60-65° C. and stirred for 2 hours at the same temperature. Cooled the reaction mixture to 25-30° C. and stirred for 5 hours at the same temperature. Filtered the precipitated solid, washed with ethyl acetate and dried to get the title compound.

Yield: 137.8 gms; M.R: 114-118° C.; Purity by HPLC: 99.96° C.

Example-3: Preparation of Mono Sodium Salt of 4-(((2S,4R)-1-([1,1'-biphenyl]-4-yl)-5-ethoxy-4-methyl-5-oxopentan-2-yl)amino)-4-oxobutanoic acid (Formula-6)

A mixture of methyl tertiary butyl ether (250 ml), tromethamine salt of 4-(((2S,4R)-1-([1,1'-biphenyl]-4-yl)-5-ethoxy-4-methyl-5-oxopentan-2-yl)amino)-4-oxobutanoic acid compound of formula-5 (50 gms) and water (150 ml) were stirred for 10 minutes at 25-30° C. Acidified the reaction mixture using aqueous hydrochloric acid solution at 25-30° C. and stirred for 15 minutes at the same temperature. Both the organic and aqueous layers were separated and aqueous layer was extracted with methyl tertiary butyl ether. Combined both the organic layers and washed with water. Distilled off the solvent completely from the organic layer under reduced pressure. Acetonitrile (125 ml) and acetone (125 ml) were added to the reaction mixture at 25-30° C. Pre-cooled aqueous sodium hydroxide solution was slowly added to the reaction mixture at 15-20° C. Raised the reaction mixture temperature to 25-30° C. and stirred for 60 minutes at 25-30° C. Distilled off the solvent completely from the reaction mixture and co-distilled with n-Heptane. Acetone (100 ml) and n-Heptane (400 ml) were added to the obtained solid at 25-30° C. and stirred for 60 minutes at the same temperature. Filtered the solid, washed with n-Heptane and dried to get the title compound.

Figure 3:
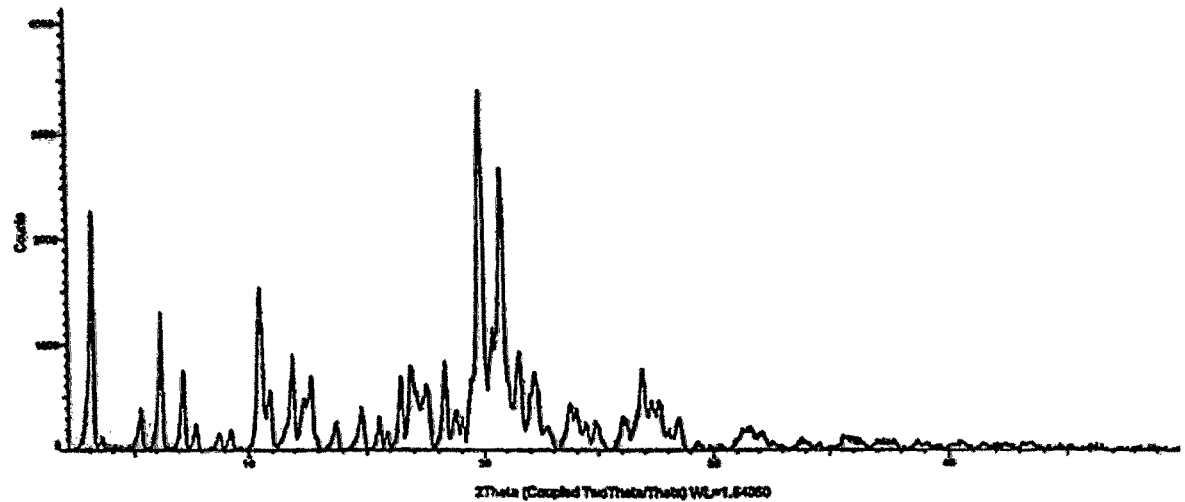
FIG. 3: Illustrates the PXRD pattern of mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 obtained according to example-3 & 10.

Yield: 17.3 gms. The PXRD pattern of the obtained compound is illustrated in FIG. 3.

Example-4: Preparation of Disodium Salt of (S)-2-(N-((2'-(1H-tetrazol-5-yl)-[1,1'-biphenyl]-4-yl)methyl)pentanamido)-3-methylbutanoic acid (Formula-7)

A mixture of valsartan (20 gms), methanol (20 ml) and acetonitrile (80 ml) were stirred for 15 minutes at 25-30° C.

Cooled the reaction mixture to 10-15° C. Aqueous sodium hydroxide solution [3.7 gm in 4.0 ml of water) was slowly added to the reaction mixture at 10-15° C. Raised the temperature of the reaction mixture to 25-30° C. and stirred for 1½ hour at the same temperature. Distilled off the solvent under reduced pressure and co-distilled with n-Heptane. To the obtained solid, n-Heptane (80 ml) and acetone (20 ml) was added at 25-30° C. and stirred for 1 hour at the same temperature. Filtered the solid, washed with n-Heptane and dried to get the title compound.

Yield: 20.2 gms; RS Purity by HPLC: 99.84%; Chiral Purity by HPLC: 99.69%.

Figure 4:
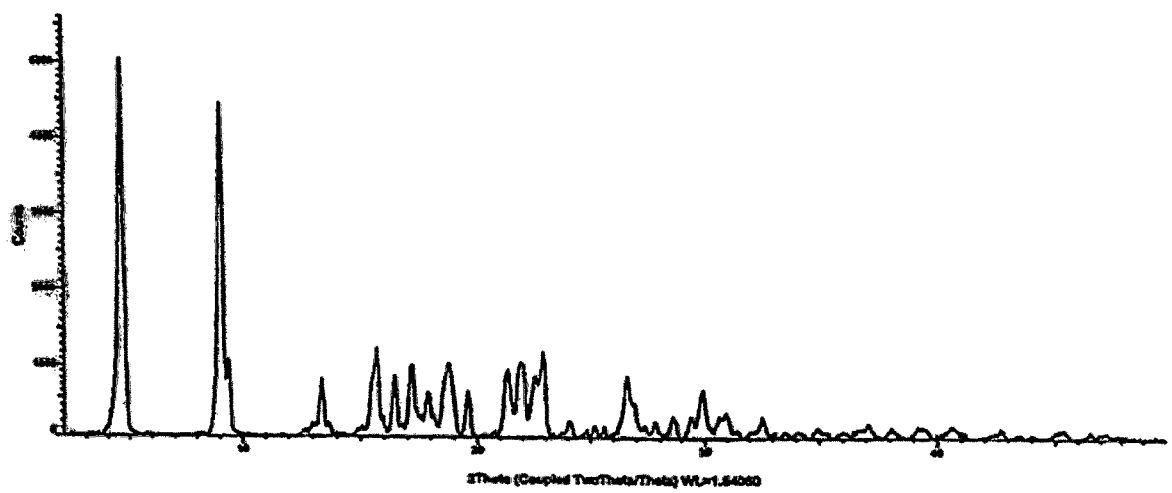
FIG. 4: Illustrates the PXRD pattern of disodium salt of (S)-2-(N-((2'-(1H-tetrazol-5-yl)-[1,1'-biphenyl]-4-yl) methyl)pentanamido)-3-methylbutanoic acid compound of formula-7 obtained according to example-4 & 11.

The PXRD pattern of the obtained compound is illustrated in FIG. 4.

Example-5: Preparation of Amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) (Formula-1)

A mixture of methanol (10 ml), water (1 ml), mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 (2 gms) and disodium salt of (S)-2-(N-((2'-(1H-tetrazol-5-yl)-[1,1'-biphenyl]-4-yl) methyl)pentanamido)-3-methylbutanoic acid compound of formula-7 (2.21 gms) were stirred for 30 minutes at 25-30° C. Filtered the reaction mixture through hyflow bed and washed with methanol. Distilled off the solvent completely from the obtained filtrate under reduced pressure to get the title compound. Yield: 3.3 gms. Particle size distribution ($D_{90}$): 157 μm.

Example-6: Preparation of Crystalline Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) (Formula-1)

A mixture of methyl tertiary butyl ether (50 ml), mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 (10 gms) and disodium salt of (S)-2-(N-((2'-(1H-tetrazol-5-yl)-[1,1'-biphenyl]-4-yl) methyl)pentanamido)-3-methylbutanoic acid compound of formula-7 (11 gms) were stirred for 45 minutes at 25-30° C. Filtered the reaction mixture and washed with methyl tertiary butyl ether and drying to get the title compound. Yield: 17.5 gms.

Figure 2:
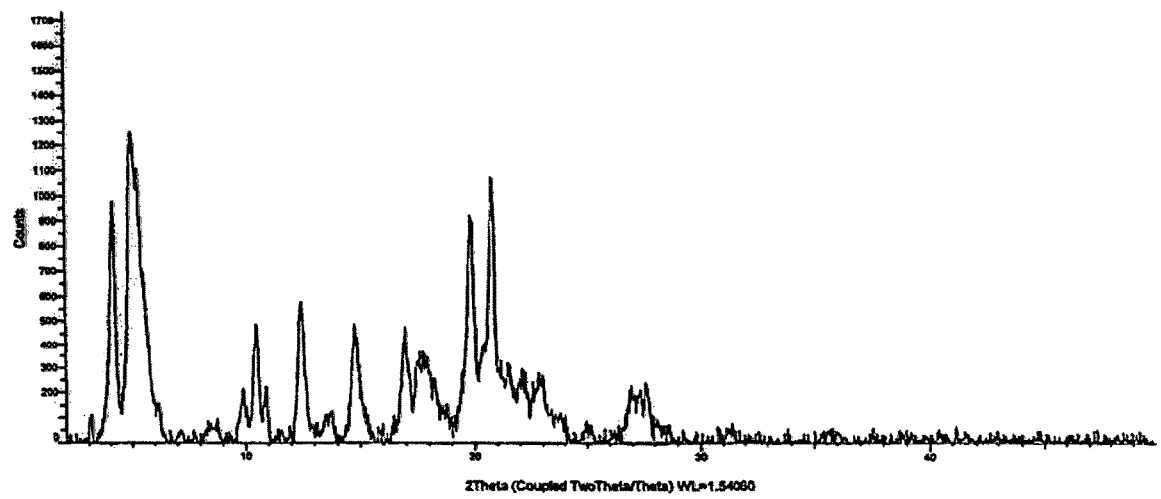
FIG. 2: Illustrates the PXRD pattern of crystalline Trisodium (4-{[(1S,3R)-1-([1,1'-biphenyl]-4-ylmethyl)-4-ethoxy-3-methyl-4-oxobutyl]amino}-4-oxobutanoate)-(N-pentano yl-N-{[2'-(1H-tetrazol-1-id-5-yl)[1,1'-biphenyl]-4-yl]methyl}-L-valinate) compound of formula-1 obtained according to example-6.

The PXRD pattern of the obtained compound is illustrated in FIG. 2.

Example-7: Preparation of Crystalline Form-M of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) (Formula-1)

A mixture of n-Heptane (50 ml), mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 (10 gms) and disodium salt of (S)-2-(N-((2'-(1H-tetrazol-5-yl)-[1,1'-biphenyl]-4-yl)methyl)pentanamido)-3-methylbutanoic acid compound of formula-7 (11 gms) were stirred for 45 minutes at 25-30° C. Filtered the reaction mixture and washed with n-Heptane and drying to get the title compound. Yield: 18.0 gms. Water content: 5-7% w/w. The PXRD pattern of the obtained compound is illustrated in FIG. 1.

Example-8: Preparation of Amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) (Formula-1)

A mixture of methyl tertiary butyl ether (500 ml), tromethamine salt of 4-(((2S,4R)-1-([1,1'-biphenyl]-4-yl)-5-ethoxy-4-methyl-5-oxopentan-2-yl)amino)-4-oxobutanoic acid compound of formula-5 (100 gms) and water (300 ml) were stirred for 10 minutes at 25-30° C. Hydrochloric acid solution (30 ml) was slowly added to the reaction mixture at 25-30° C. and stirred for 15 minutes at the same temperature. Both the organic and aqueous layers were separated and aqueous layer was extracted with methyl tertiary butyl ether. Combined the organic layers and washed with water. Distilled off the solvent completely from the organic layer under reduced pressure.

Methanol (100 ml) was added to the obtained residue at 15-20° C. (S)-2-(N-((2'-(1H-tetrazol-5-yl)-[1,1'-biphenyl]-4-yl)methyl)pentanamido)-3-methylbutanoic acid compound of formula-8 (81.8 gms) and acetonitrile (500 ml) were added to the reaction mixture at 25-30° C. and stirred for 15 minutes at the same temperature. Pre-cooled aqueous sodium hydroxide solution [21.0 gms of sodium hydroxide dissolved in 250 ml of water] was slowly added to the reaction mixture at 15-20° C. Raised the reaction mixture temperature to 25-30° C. and stirred for 4 hours at the same temperature. Filtered the reaction mixture through hyflow bed and washed with methanol. Distilled off the solvent from the obtained filtrate and co-distilled with acetonitrile under reduced pressure. Acetonitrile (500 ml) was added to the obtained compound at 25-30° C. and stirred for 60 minutes at the same temperature. Filtered the solid and washed with acetonitrile under nitrogen atmosphere.

Methanol (500 ml) and water (50 ml) were added to the obtained wet compound at 25-30° C. and stirred for 30 minutes at the same temperature. Filtered the reaction mixture through hyflow bed and washed with methanol. Distilled off the solvent completely from the obtained filtrate under reduced pressure to get the title compound. Yield: 140 gms.

Example-9: Preparation of Crystalline Form-S of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) (Formula-1)

A mixture of n-Heptane (150 ml), mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 (25 gms) and disodium salt of (S)-2-(N-((2'-(1H-tetrazol-5-yl)-[1,1'-biphenyl]-4-yl)methyl)pentanamido)-3-methylbutanoic acid compound of formula-7 (27.65 gms) were stirred for 2 hours at 0-5° C. under nitrogen atmosphere. Filtered the solid and washed with n-Heptane under nitrogen atmosphere. Drying the solid under reduced pressure to get the title compound. Yield: 54.4 gms. Water content: 5.9% w/w.

Particle size distribution ($D_{90}$)<50 μm.

The PXRD pattern of the obtained compound is illustrated in FIG. 5.

Example-10: Preparation of Mono Sodium Salt of 4-(((2S,4R)-1-([1,1'-biphenyl]-4-yl)-5-ethoxy-4-methyl-5-oxopentan-2-yl)amino)-4-oxobutanoic acid (Formula-6)

A mixture of methyl tertiary butyl ether (500 ml), tromethamine salt of 4-(((2S,4R)-1-([1,1'-biphenyl]-4-yl)-5-ethoxy-4-methyl-5-oxopentan-2-yl)amino)-4-oxobutanoic acid compound of formula-5 (100 gms) and water (300 ml) were stirred for 10 minutes at 25-30° C. Acidified the reaction mixture using aqueous hydrochloric acid solution at 25-30° C. and stirred for 15 minutes at the same temperature. Both the organic and aqueous layers were separated and aqueous layer was extracted with methyl tertiary butyl ether. Combined both the organic layers and washed with water. Distilled off the solvent completely from the organic layer under reduced pressure to get compound of formula-4 as a residue.

Acetonitrile (100 ml) was added to the obtained residue at 15-20° C. Pre-cooled aqueous sodium hydroxide solution was slowly added to the reaction mixture at 15-20° C. Raised the reaction mixture temperature to 25-30° C. and stirred for 90 minutes at 25-30° C. Filtered the reaction mixture and washed with acetonitrile. Distilled off the solvent completely from the filtrate and co-distilled with methyl tertiary butyl ether. Methyl tertiary butyl ether (800 ml) was added to the obtained solid at 25-30° C. and stirred for 90 minutes at the same temperature. Filtered the solid, washed with methyl tertiary butyl ether and dried to get the title compound. Yield: 70.0 gms. Melting Range: 140 to 150° C.

The PXRD pattern of the obtained compound is illustrated in FIG. 3.

Example-11: Preparation of Disodium Salt of (S)-2-(N-((2'-(1H-tetrazol-5-yl)-[1,1'-biphenyl]-4-yl)methyl)pentanamido)-3-methylbutanoic acid (Formula-7)

A mixture of valsartan (100 gms) and acetone (300 ml) were stirred for 15 minutes at 25-30° C. Cooled the reaction mixture to 10-15° C. Aqueous sodium hydroxide solution [17.4 gm in 18 ml of water) was slowly added to the reaction mixture at 10-15° C. Raised the temperature of the reaction mixture to 25-30° C. and stirred for 3 hours at the same temperature. Filtered the reaction mixture and washed with acetone. Acetone (1000 ml) and seeding material of compound of formula-7 were added to the filtrate at 25-30° C. Cooled the reaction mixture to 15-20° C. and stirred for 15 hours at the same temperature. Filtered the solid, washed with acetone and dried to get the title compound.

Yield: 98.0 gms; Melting Range: 240 to 250° C.
The PXRD pattern of the obtained compound is illustrated in FIG. 4.

Example-12: Preparation of Crystalline Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) hemipentahydrate A mixture of acetonitrile (200 ml), mono sodium salt of 4-(((2S,4R)-1-([1,1'-biphenyl]-4-yl)-5-ethoxy-4-methyl-5-oxopentan-2-yl)amino)-4-oxobutanoic acid compound of formula-6 (50 gms) and disodium salt of (S)-2-(N-((2'-(1H-tetrazol-5-yl)-[1,1'-biphenyl]-4-yl)methyl)pentanamido)-3-methylbutanoic acid compound of formula-7 (55.3 gms) were stirred for 10 minutes at 25-30° C. Methanol (50 ml) and water (25 ml) were added to the reaction mixture and stirred for 1½ hours at 25-30° C. Filtered the reaction mixture and washed with methanol. Distilled-off the solvent completely from the obtained filtrate under reduced pressure and co-distilled with acetonitrile. Acetonitrile (250 ml) was added to the obtained solid and stirred the reaction mixture for 1 hour at 25-30° C. Filtered the solid and washed with acetonitrile and drying to get the title compound. Yield: 106.0 gms. Melting range: 134-138° C. Water content: 4.0% to 6.0% w/w.

The PXRD pattern of the obtained compound is similar to the crystalline Trisodium Sacubitril Valsartan hemipentahydrate disclosed in U.S. Pat. No. 8,877,938B2.

Example-13: Preparation of Amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl] methyl}-L-valinate) (Formula-1)

Methanol (500 ml) and water (50 ml) were added to the compound of formula-1 (100 gms) at 25-30° C. and stirred for 30 minutes at the same temperature. Filtered the reaction mixture through hyflow bed and washed with methanol. Distilled off the solvent completely from the obtained filtrate under reduced pressure to get the title compound. Yield: 95.0 gms. Particle size distribution ($D_{90}$): 157 μm.

Example-14: Preparation of Amorphous Form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) Compound of Formula-1

A mixture of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 (10 gms) and methanol (300 ml) were stirred for 10 minutes at 25-30° C. to get a clear solution. Filtered the resulting solution and distilled off the solvent completely from the filtrate under reduced pressure and dried to get the title compound. Yield: 7.6 gms.

Figure 7:
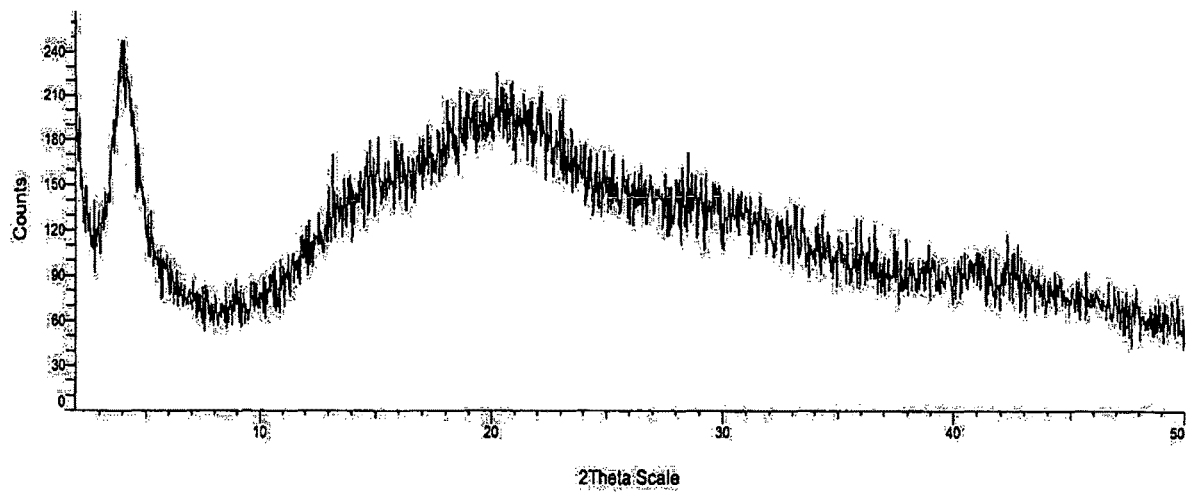
FIG. 7: Illustrates the PXRD pattern of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentano yl-N-{[2'-(1H-tetrazol-1-id-5-yl)[1,1'-biphenyl]-4-yl]methyl}-L-valinate) compound of formula-1 obtained according to example-14.

The PXRD pattern of the obtained compound is shown in FIG. 7.

Example-15: Preparation of Amorphous Form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) Compound of Formula-1

A mixture of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 (0.5 gms), methanol (10 ml) and dichloromethane (10 ml) were stirred for 10 minutes at 25-30° C. to get a clear solution. Filtered the resulting solution and distilled off the solvent completely from the filtrate under reduced pressure and then dried the material to get the title compound.

Figure 8:
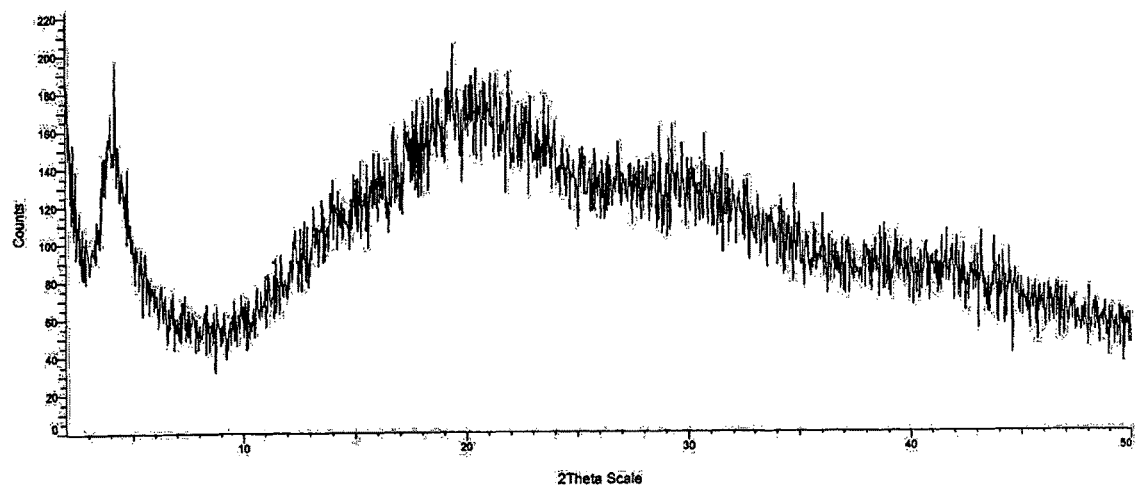
FIG. 8: Illustrates the PXRD pattern of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentano yl-N-{[2'-(1H-tetrazol-1-id-5-yl)[1,1'-biphenyl]-4-yl]methyl}-L-valinate) compound of formula-1 obtained according to example-15.

Yield: 0.4 gms. The PXRD pattern of the obtained compound is shown in FIG. 8.

Example-16: Preparation of Amorphous Form of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) Compound of Formula-1

A mixture of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 (5 gms) and methanol (100 ml) were stirred for 15 min at 25-30° C. to get a clear solution. Filtered the resulting solution at 25-30° C. and the obtained clear solution was spray dried under following conditions.

Figure 9:
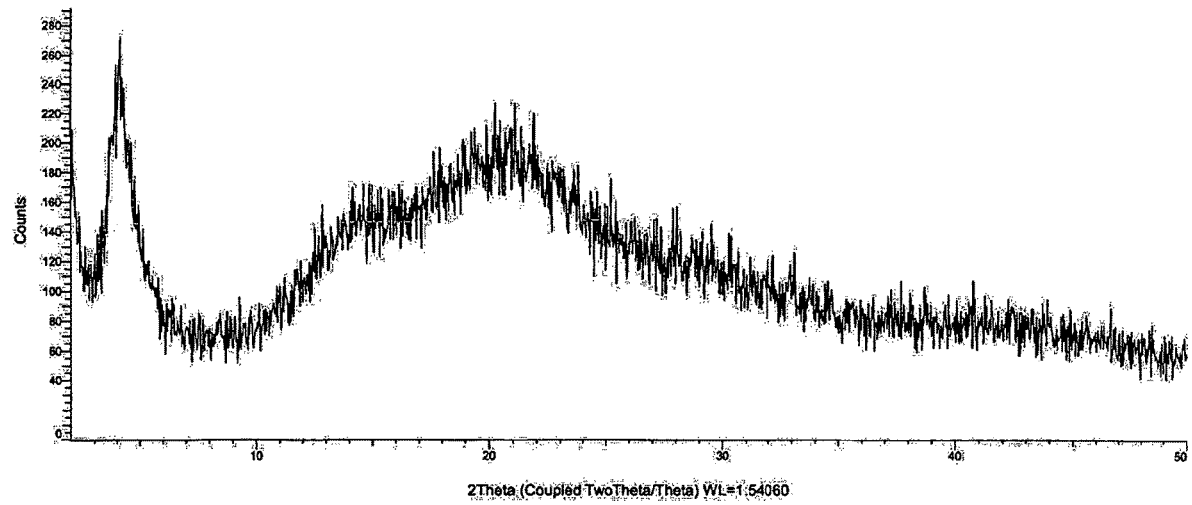
FIG. 9: Illustrates the PXRD pattern of amorphous Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 obtained according to example-16.

Inlet temperature: 60° C.
Feed rate: 10 ml/min
Aspirator flow rate: 70%
Nitrogen pressure: 2.0 kg The obtained solid was collected from the spray dryer and dried at 40-45° C. under vacuum to get the title compound. Yield: 3.2 gms
The PXRD pattern of the obtained compound is shown in FIG. 9.

Example-17: Preparation of Amorphous Solid Dispersion Comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) and Polyvinyl Pyrrolidine-K-30: (1:1)

Figure 10:
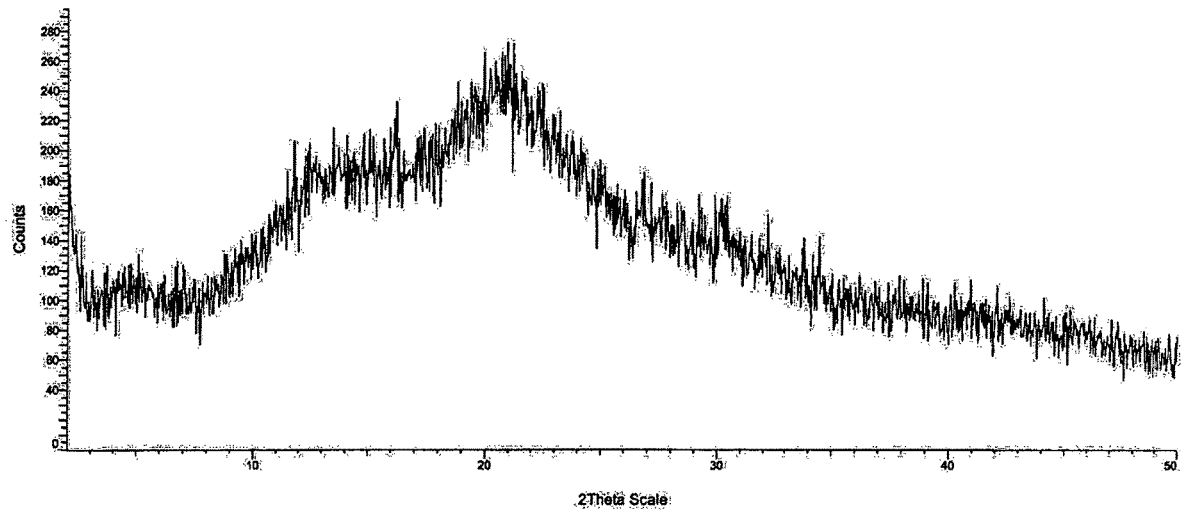
FIG. 10: Illustrates the PXRD pattern of amorphous solid dispersion comprising Trisodium (4-{[(1S,3R)-1-([1,1'-biphenyl]-4-ylmethyl)-4-ethoxy-3-methyl-4-oxobutyl] amino}-4-oxobutanoate)-(N-pentanoyl-N-{[2'-(1H-tetrazol-1-id-5-yl)[1,1'-biphenyl]-4-yl]methyl}-L-valinate) compound of formula-1 and PVP-K-30.

A mixture of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 (0.5 gms), polyvinyl pyrrolidine-K-30 (0.5 gms), methanol (20 ml) and dichloromethane (20 ml) were stirred for 10 minutes at 25-30° C. to get a clear solution. Filtered the resulting solution and distilled off the solvent completely from the filtrate under reduced pressure and then dried the material to get the title compound. Yield: 0.8 gms.
The PXRD pattern of the obtained compound is shown in FIG. 10.

Example-18: Preparation of Amorphous Solid Dispersion Comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) and Hydroxypropyl Methylcellulose (HPMC): (1:1)

A mixture of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 (0.5 gms), hydroxypropyl methylcellulose (0.5 gms), methanol (20 ml) and dichloromethane (20 ml) were stirred for 10 minutes at 25-30° C. to get a clear solution. Filtered the resulting solution and distilled off the solvent completely from the filtrate under reduced pressure and then dried the material to get the title compound. Yield: 0.6 gms.

Figure 11:
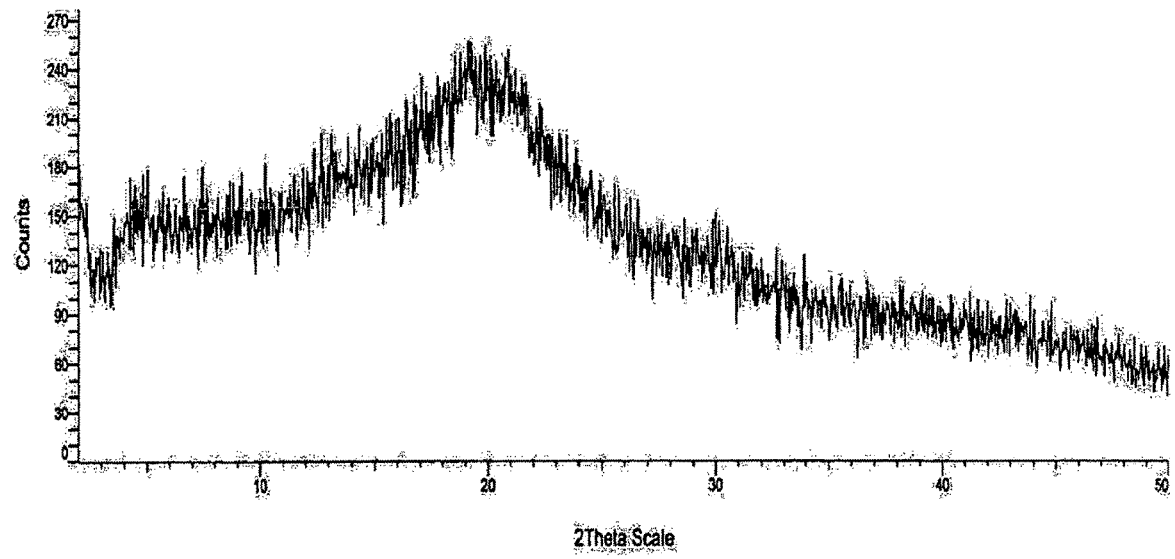
FIG. 11: Illustrates the PXRD pattern of amorphous solid dispersion comprising Trisodium (4-{[(1S,3R)-1-([1,1'-biphenyl]-4-ylmethyl)-4-ethoxy-3-methyl-4-oxobutyl] amino}-4-oxobutanoate)-(N-pentanoyl-N-{[2'-(1H-tetrazol-1-id-5-yl)[1,1'-biphenyl]-4-yl]methyl}-L-valinate) compound of formula-1 and HPMC.

The PXRD pattern of the obtained compound is shown in FIG. 11.

Example-19: Preparation of Amorphous Solid Dispersion Comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) and Hydroxypropyl Methylcellulose Acetate Succinate (HPMC-AS): (1:1)

A mixture of Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 (0.5 gms), hydroxypropyl methylcellulose acetate succinate (0.5 gms), methanol (20 ml) and dichloromethane (20 ml) were stirred for 10 minutes at 25-30° C. to get a clear solution. Filtered the resulting solution and distilled off the solvent completely from the filtrate under reduced pressure and then dried the material to get the title compound. Yield: 0.8 gms.

Figure 12:
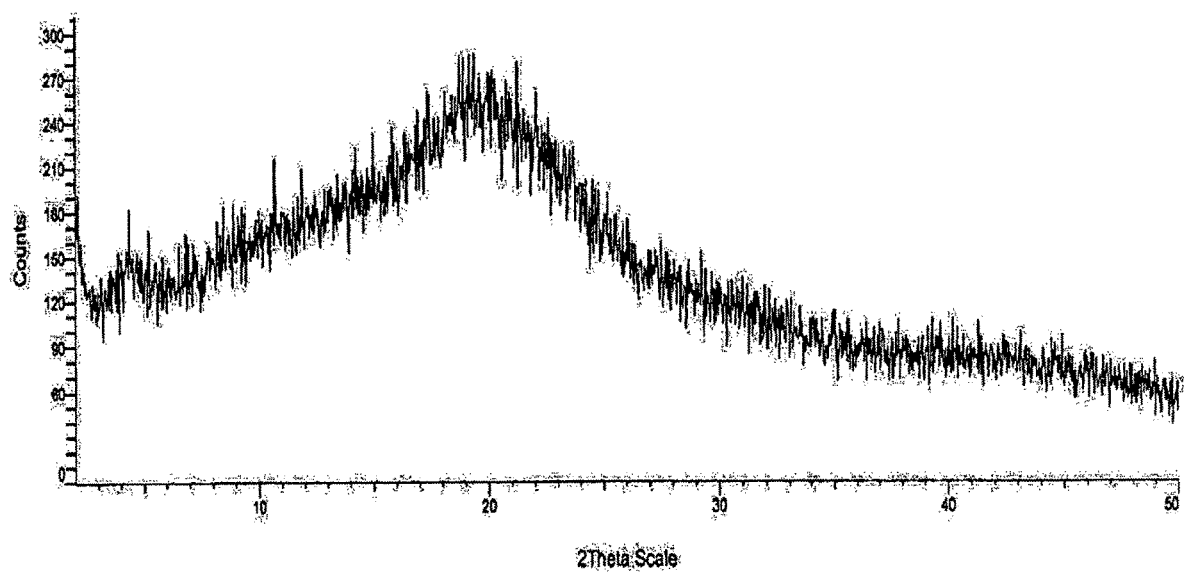
FIG. 12: Illustrates the PXRD pattern of amorphous solid dispersion comprising Trisodium (4-{[(1S,3R)-1-([1,1'-biphenyl]-4-ylmethyl)-4-ethoxy-3-methyl-4-oxobutyl] amino}-4-oxobutanoate)-(N-pentanoyl-N-{[2'-(1H-tetrazol-1-id-5-yl)[1,1'-biphenyl]-4-yl]methyl}-L-valinate) compound of formula-1 and HPMCAS.

The PXRD pattern of the obtained compound is shown in FIG. 12.

Example-20: Preparation of Amorphous Solid Dispersion Comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) and Hydroxypropyl Cellulose (HPC): (1:1)

A mixture of Trisodium (4-{[(1S,3R)-1-([1,1'-biphenyl]-4-ylmethyl)-4-ethoxy-3-methyl-4-oxobutyl]amino})-4-oxobutanoate)-(N-pentanoyl-N-{[2'-(1H-tetrazol-1-id-5-yl)[1,1'-biphenyl]-4-yl]methyl}-L-valinate) compound of formula-1 (0.5 gms), hydroxyl propylcellulose (0.5 gms), methanol (20 ml) and dichloromethane (20 ml) were stirred for 10 minutes at 25-30° C. to get a clear solution. Filtered the resulting solution and distilled off the solvent completely from the filtrate under reduced pressure and then dried the material to get the title compound.

Yield: 0.6 gms.

Figure 13:
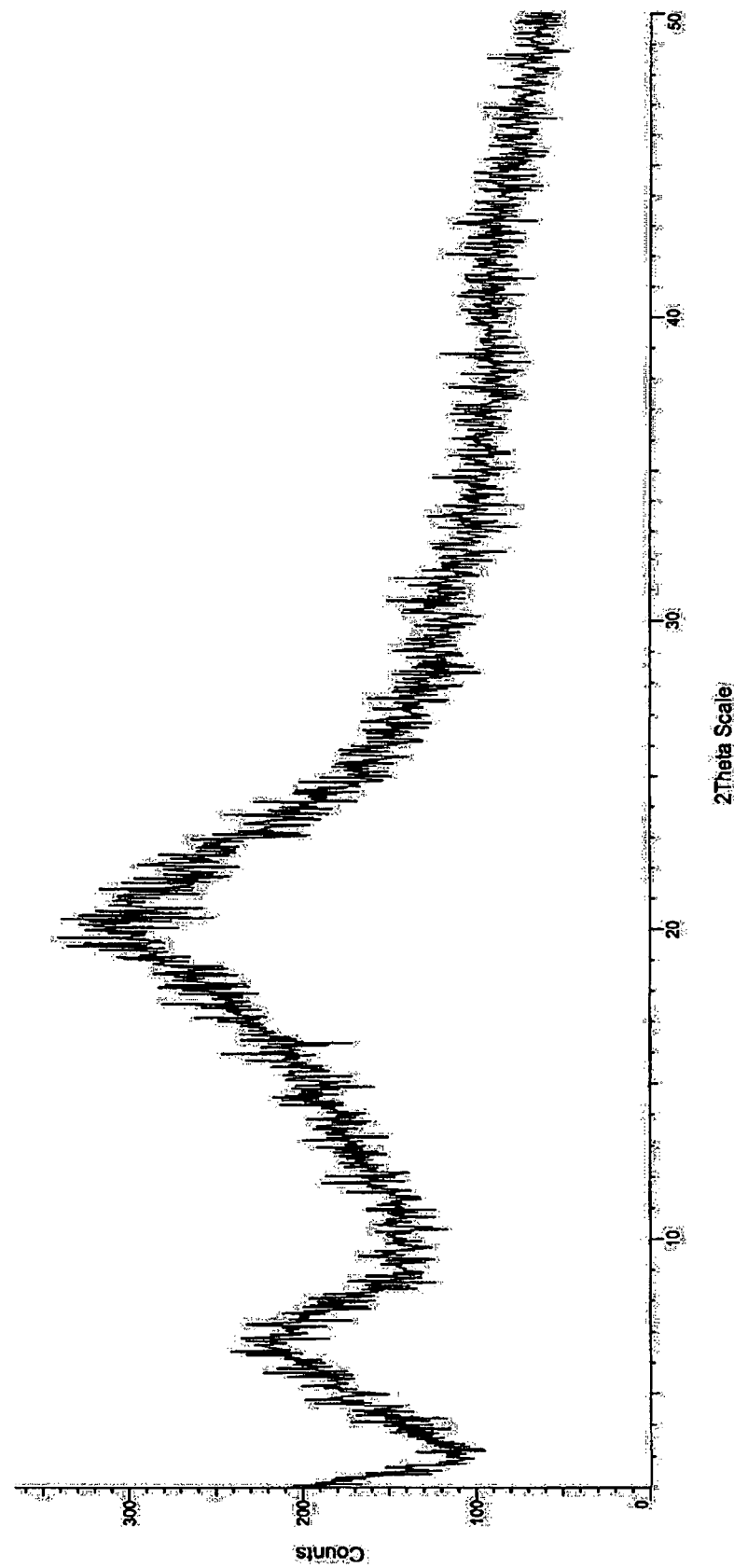
FIG. 13: Illustrates the PXRD pattern of amorphous solid dispersion comprising Trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1 and HPC.

The PXRD pattern of the obtained compound is shown in FIG. 13.

We claim:

1. A process for the preparation of trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) compound of formula-1,

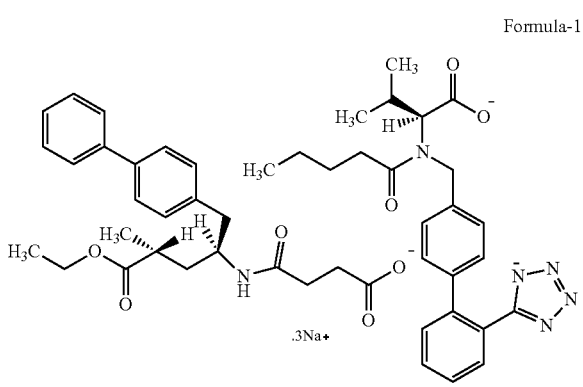 [SMILES: CCOC(=O)[C@H](C)C[C@@H](Cc1ccc(-c2ccccc2)cc1)NC(=O)CCC(=O)[O-] ; CCCCC(=O)N(Cc1ccc(-c2ccccc2-c2nnn[n-]2)cc1)[C@H](C(=O)[O-])C(C)C]

comprising:
a) reacting mono sodium salt of 4-(((2S,4R)-1-([1,1'-biphenyl]-4-yl)-5-ethoxy-4-methyl-5-oxopentan-2-yl)amino)-4-oxobutanoic acid of formula-6

Formula-6 with disodium salt of (S)-2-(N-((2'-(1H-tetrazol-5-yl)-[1,1'-biphenyl]-4-yl)methyl)pentanamido)-3-methylbutanoic acid of formula-7

Formula-7 in a solvent,
b) obtaining trisodium salt of (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) of formula-1 by removal of the solvent.

2. The process according to claim 1, wherein the solvent in step-a) is selected from alcohol solvents, ketone solvents, ester solvents, hydrocarbon solvents, nitrile solvents, ether solvents, chloro solvents, polar aprotic solvents, water or mixture thereof.

3. The process according to claim 1, wherein removal of the solvent in step-b) is carried out by a method selected from the group consisting of filtration, evaporation, evaporation under reduced pressure, flash evaporation, vacuum drying, concentrating the mixture, atmospheric distillation, vacuum distillation distillation by using a rotational distillation device such as a Buchi Rotavapor, agitated thin film drying (ATM), melt extrusion, spray drying, freeze drying (lyophilization), spray-freeze diving, addition of suitable anti-solvent to the reaction mixture followed by filtration of the precipitated solid, and cooling the clear solution to lower temperatures such as below 20° C. to precipitate the solid followed by filtration.

4. The process according to claim 1, wherein the process comprises:
a) reacting formula-6 with formula-7 in aqueous methanol; and
b) removing solvent from the mixture of step a) to obtain amorphous form of formula-1.

5. The process according to claim 1, wherein the process comprises:
a) reacting formula-6 with formula-7 in methanol, water and acetonitrile;
b) optionally stirring the mixture,
c) removing solvent from the mixture of step a) or step-b); and
d) obtaining crystalline trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate)hemipentahydrate by adding acetonitrile.

6. The process according to claim 1, wherein the process comprises:
a) reacting formula-6 with formula-7 in acetonitrile,
b) optionally stirring the mixture, and
c) obtaining crystalline trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) hemipentahydrate by removal of solvent.

7. The process according to claim 1, wherein the process comprises:
a) reacting the formula-6 with formula-7 in a hydrocarbon solvent, and
b) obtaining crystalline Form-S of formula-1.

8. The process according to claim 7, wherein the hydrocarbon solvent is selected from the group consisting of n-pentane, n-hexane, n-heptane, cyclohexane, pet ether, benzene, toluene and xylene.

9. A Crystalline Form-S of trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) of formula-1, having an X-ray powder diffraction pattern showing characteristic peaks at 3.1, 4.6, 9.2 and 11.80±0.2° 2-theta.

10. The Crystalline Form-S of claim 9, having an X-ray powder diffraction pattern further comprising peaks at 6.2, 7.2, 10.5, 12.5, 12.8, 15.8, 16.5, 17.5, 18.4, 18.8, 19.9, 20.8, 21.3, 21.9, 22.3 and 25.0±0.2° 2-theta.

11. Crystalline Form-S of claim 9, having an X-ray powder diffraction pattern further comprising peaks as illustrated in figure-5.

12. A pharmaceutical composition comprising:
crystalline Form-S of trisodium (4-{[(1S,3R)-1-([1,1'-biphenyl]-4-ylmethyl)-4-ethoxy-3-methyl-4-oxobutyl]amino}-4-oxobutanoate)-(N-pentanoyl-N-{[2'-(1H-tetrazol-1-id-5-yl)[1,1'-biphenyl]-4-yl]methyl}-L-valinate) of claim 9; and a pharmaceutically acceptable carrier.

* * * * *